(12) United States Patent
Trautzsch et al.

(10) Patent No.: US 9,869,640 B2
(45) Date of Patent: Jan. 16, 2018

(54) METHOD AND DEVICE FOR EXAMINING A MASK

(71) Applicant: Carl Zeiss SMT GmbH, Oberkochen (DE)

(72) Inventors: Thomas Trautzsch, Jena (DE); Ute Buttgereit, Jena (DE); Thomas Thaler, Dresden (DE)

(73) Assignee: Carl Zeiss SMT GmbH, Oberkochen (DE)

( * ) Notice: Subject to any disclaimer, the term of this patent is extended or adjusted under 35 U.S.C. 154(b) by 219 days.

(21) Appl. No.: 14/563,259

(22) Filed: Dec. 8, 2014

(65) Prior Publication Data

US 2015/0198541 A1 Jul. 16, 2015

(30) Foreign Application Priority Data

Dec. 10, 2013 (DE) .............................. 10201302075

(51) Int. Cl.
*G01N 21/95* (2006.01)
*G03F 1/84* (2012.01)
(Continued)

(52) U.S. Cl.
CPC ......... *G01N 21/9505* (2013.01); *G01N 21/17* (2013.01); *G01N 21/8851* (2013.01);
(Continued)

(58) Field of Classification Search
CPC ............... G01N 21/9505; G01N 21/17; G01N 21/8851; G01N 21/956; G01N 2021/1765;
(Continued)

(56) References Cited

U.S. PATENT DOCUMENTS

2004/0235205 A1* 11/2004 Levy .................... G01N 21/211
438/14
2005/0002554 A1 1/2005 Schulze et al.
(Continued)

FOREIGN PATENT DOCUMENTS

| DE | 10 2004 031 877 | 3/2005 | ........... G01N 21/956 |
| DE | 10 2009 038 558 | 3/2011 | ............... G03F 7/20 |
| WO | WO 2013179956 A1 * | 12/2013 | ............. G01B 15/04 |

OTHER PUBLICATIONS

H.H. Hopkins: On the diffraction theory of optical images. Proceedings of the Royal Society of London. Series A, Mathematical and Physical Sciences, 217 (1130): 408-432, (1953).

(Continued)

*Primary Examiner* — Amandeep Saini
(74) *Attorney, Agent, or Firm* — Fish & Richardson P.C.

(57) ABSTRACT

A method for examining a mask includes providing a position data set having error positions of the mask to be examined, providing a structure data set having the structure of the mask, and specifying structural features of the mask, the values of which are to be determined. At each error position, determining the values of the specified structural features of the structure by using a computing unit, determining a measuring task from specified decision criteria and from the determined values of the structural features of the structure by using the computing unit, and carrying out the determined measuring task in a manner controlled by the computing unit. In addition, a device, in particular a microscope, for carrying out the method is provided.

20 Claims, 6 Drawing Sheets

(51) Int. Cl.
*G01N 21/956* (2006.01)
*G01N 21/17* (2006.01)
*G01N 21/88* (2006.01)
*G06K 9/00* (2006.01)
*G06T 7/00* (2017.01)
*G06T 7/60* (2017.01)

(52) U.S. Cl.
CPC .............. *G01N 21/956* (2013.01); *G03F 1/84* (2013.01); *G06K 9/00134* (2013.01); *G06T 7/0004* (2013.01); *G06T 7/60* (2013.01); *G01N 2021/1765* (2013.01); *G01N 2021/8887* (2013.01); *G01N 2021/95676* (2013.01)

(58) Field of Classification Search
CPC .. G01N 2021/8887; G01N 2021/95676; G03F 1/84; G06K 9/00134; G06T 7/0004; G06T 7/60
USPC ........................................................ 382/144
See application file for complete search history.

(56) References Cited

U.S. PATENT DOCUMENTS

| 2007/0172111 | A1 | 7/2007 | Ikeda |
| 2009/0059208 | A1* | 3/2009 | Steffens ............. G01B 11/2441 356/73 |
| 2009/0180680 | A1 | 7/2009 | Satou et al. |
| 2011/0090329 | A1 | 4/2011 | Poortinga et al. |
| 2011/0242544 | A1* | 10/2011 | Stroessner ................ G03F 1/84 356/496 |
| 2011/0243424 | A1* | 10/2011 | Wu .......................... G03F 1/84 382/144 |
| 2012/0243772 | A1* | 9/2012 | Yamanaka ................ G03F 1/86 382/144 |

OTHER PUBLICATIONS

Dargestellt sind. Für die Simulation von Luftbildern von Masken ist beispielsweise das Programm MicroSim erhältlich. Die Simulation erfolgt ausgend von den Strukturvorgaben der Maske, dem Masken-Design. Das Programm MicroSim wird beispielsweise beschrieben in: M. Totzeck, "Numerical simulation of high-NA quantitative polarization microscopy and corresponding near-fields," Optik, 112 (2001) 381-390, (MicroSim-Software, University of Stuttgart).

* cited by examiner

METHOD AND DEVICE FOR EXAMINING A MASK

CROSS-REFERENCE TO RELATED APPLICATION

Under 35 U.S.C. §119, this application claims priority to German Patent Application 10 2013 020 705.3, filed on Dec. 10, 2013, whose disclosure content is hereby incorporated by reference in its entirety.

TECHNICAL FIELD

The invention relates to a method and a device for examining a mask.

BACKGROUND

The requirements for masks, which are used in lithography for producing structures on wafers, are increasing continuously. The dimensions of the structures on the masks become smaller and smaller with each development step. This has the result that the production process becomes more and more complex and the masks become more susceptible to defects. This applies both to transmissive masks and also to reflective masks. The susceptibility to defects during the production of reflective masks is very high in comparison to transmissive masks because of their complex structure and even smaller dimensions of the structures.

SUMMARY

Masks are regularly examined for defected regions for quality control directly after production, but also during use. In this case, the structure produced on the mask can be completely checked. This is referred to as mask inspection. During the mask inspection, a rapid check of the structure of the mask for defects is performed. The positions thus found, which are marked as defected, are stored in a position data set and checked in a further step by further, more precise measuring devices. It is then examined whether the defects found are relevant during use of the mask. This is referred to as the mask review. The relevant defects are then repaired in a repair device.

Alternatively or additionally, positions can be derived from the mask structure, at which defects occur particularly frequently during the production of a mask, so-called hot spots. These positions are stored as defect positions in a position data set. A mask inspection or a mask review can be performed at the determined positions.

The mask inspection is carried out, for example, using a device of the Teron 600 series from KLA-Tencor or a device of the designation WLCD from Carl Zeiss SMS GmbH. For example, a device of the designation AIMS from Carl Zeiss SMS can be used for the mask review.

The coordinates of positions which are classified as defected in a mask structure are stored in a position data set. The coordinates of these defect positions refer to the mask structure, which is also referred to as the mask design or mask layout. A mask structure is provided as a computer readable structure data set.

The type of the further examination, i.e., a measuring task, is to be defined for each defect position. This can relate to the selection of a probe to be used, or also the steps which are to be performed during the measurement at a position by a respective probe. For example, if aerial images of the structures at the defect positions are recorded for the further examination, it is thus to be defined for the various structure types which parameters of the individual aerial images are to be measured.

A first step in the examination of masks is the assignment of the respective measurement task to a defect position. In this case, for each defect position, the respective structure type of the mask structure can be determined. A suitable measurement task can be selected for each structure type.

The number of the defect positions on a mask is generally very high and increases with each generation of newly developed masks. A high degree of automation is therefore necessary for checking and examining the mask.

The object of the invention is therefore to increase the degree of automation of the examination of masks.

This object is achieved according to the invention by a method for examining a mask comprising the following steps:
providing a position data set having defect positions of the mask to be examined; providing a structure data set having the structure of the mask;
specifying structural features of the mask which are to be determined;
at each defect position: determining the values of the predefined structural features of the structure by way of a computing unit; determining a measuring task from predefined decision criteria and the determined values of the structural features of the structure by way of the computing unit; carrying out the determined measuring task in a manner controlled by the computing unit.

A mask structure is also referred to as a mask design. In this data set, it is established in the case of transmissive masks which regions of the mask surface are light-transmissive or light-opaque. For reflective masks, it is specified which regions are embodied as reflective or absorbent for the illumination radiation.

A measuring task can comprise a single step or also multiple steps. These steps can comprise performing measurements using one or more measuring methods or the analysis of measurement results.

The computing unit for carrying out the method can be implemented as a computer, on which a computer program is executed. The computing unit is embodied or programmed for carrying out the corresponding method steps.

This measure has the advantage that the examination of a mask, proceeding from specified defect positions up to carrying out a measuring task, can be carried out automatically, i.e., controlled by a computing unit. In addition, decision criteria for checking a mask structure can be rapidly checked and optimized.

A measuring task is determined by the computing unit for each defect position by processing the data of the structure data set and the predefined decision criteria. The decision criteria can be specified as a correlation data set, or can be specified by an algorithm of the computer program running on the computing unit.

The assignment of structure types or measuring tasks to defect positions is also referred to as marking the structure or as setting markers.

In a further embodiment of the invention, a correlation data set having decision criteria is provided, which comprises an assignment of structural features of the structure to the measuring task.

This measure has the advantage that the decision criteria can be provided and changed in a simple manner. The preparation of a program by the user is no longer necessary.

In a further variant of this embodiment of the invention, the correlation data set comprises the assignment of structural features of the structure to structure types and the assignment of a measuring task to each structure type.

This measure is advantageous if the measuring task can be defined directly on the basis of the structure type and the same measuring task is to be carried out for all structures of a type.

In a further embodiment of the invention, measuring tasks are determined by a script of the CATS software, which is executed in the computing unit.

This measure has the advantage that such a script can be prepared and changed in a simple manner.

In a further embodiment of the invention, a script for determining the measuring tasks is prepared from the correlation data set by the computing unit.

This measure enables the rapid implementation of the decision criteria from the correlation data set.

In a further embodiment of the invention, a measuring task comprises recording an aerial image using a microscope.

For the microscope, a microscope which is specially optimized for examining masks can be used, for example, the mentioned devices of the designation WLCD or AIMS. Other optical microscopes or other atomic force microscopes or scanning tunneling microscopes can also be used, for example.

In a further embodiment of the invention, the defect positions of the position data set are determined by carrying out a mask inspection.

In a further embodiment of the invention, the defect positions of the position data set comprise hot spots of the structure.

In a further embodiment of the invention, each defect position is assigned to a measurement region.

This method has the advantage that the examination is restricted to the required regions. This results in a time savings.

In a further embodiment of the invention, to determine the structural features of a structure from the respective structure data set, an aerial image of the assigned measurement region is stimulated, wherein the structural features are determined by an analysis of the aerial image by a computing unit.

This measure has the advantage that structural features can be determined in a form as they occur on the wafer during the exposure of the structures. Thus, for example, in the case of structures which contain OPC features to increase the resolution, a direct determination of some structural features is not possible. This is also the case for so-called SMO structures.

In a further embodiment of the invention, at least the value of one of the following structural features is determined: critical dimension, tone, edge length, length of a line, aspect ratio of length and width.

The tone of a mask can assume the values transparent or opaque. In the case of transmissive masks, for example, made of a structure of a chromium layer on glass, the structural feature tone having the value transparent means that no chromium layer is applied here to the glass of the mask. The mask is transmissive to illumination radiation here. The value opaque means that a chromium layer is applied. The mask is opaque to illumination radiation here. In the case of reflective masks, the value transparent means that the mask reflects illumination radiation and the value opaque means that the mask absorbs, i.e., does not reflect, the illumination radiation. The determination of the value of the tone is preferably performed in the center point of a measurement region.

This measure has the advantage that these structural features are to be determined in a simple manner.

In a further embodiment of the invention, at least the following structure types are assignable: lines and spaces, contact hole, end-to-end.

This measure has the advantage that these structure types are present in numerous structures.

The invention additionally comprises a computer-implemented method for assigning measuring tasks to defect positions of a mask comprising the following steps:

providing a position data set having defect positions of the mask to be examined;

providing a structure data set having the structure of the mask;

specifying structural features of the mask which are to be determined;

at each defect position: determining the values of the specified structural features of the structure by way of a computing unit; determining a measuring task from specified decision criteria and from the determined values of the structural features of the structure by way of the computing unit.

The invention additionally comprises a device for examining a mask having a computing unit which is embodied for carrying out the method.

In a further embodiment of the invention, the device is implemented as a microscope. The microscope can be a device specialized for examining masks, for example, an AIMS or a WLCD.

The invention additionally comprises a microscope having an imaging optic for imaging the structure of the mask at defect positions, a detector for recording an aerial image of the structure of the mask at the defect positions;

a computing unit, which is embodied to carry out the method comprising the following steps:

providing a position data set having defect positions of the mask to be examined;

providing a structure data set having the structure of the mask;

providing structural features of the mask, the values of which are to be determined;

at each defect position: determining the values of the specified structural features of the structure by way of a computing unit, determining a measuring task from specified decision criteria and the determined values of the structural features of the structure by way of the computing unit, recording of the aerial image in a manner controlled by the computing unit, in accordance with the determined measuring task, execution of an analysis of the aerial image in accordance with the determined measuring task.

It is apparent that the above-mentioned features of the invention and the features still to be explained hereafter can be used not only in the described combinations, but rather also in further combinations or alone, without leaving the scope of the present invention.

BRIEF DESCRIPTION OF DRAWINGS

The invention will be described and explained in greater detail hereafter on the basis of several selected exemplary embodiments and on the basis of the drawings.

In the figures.

DETAILED DESCRIPTION

Figure 1:
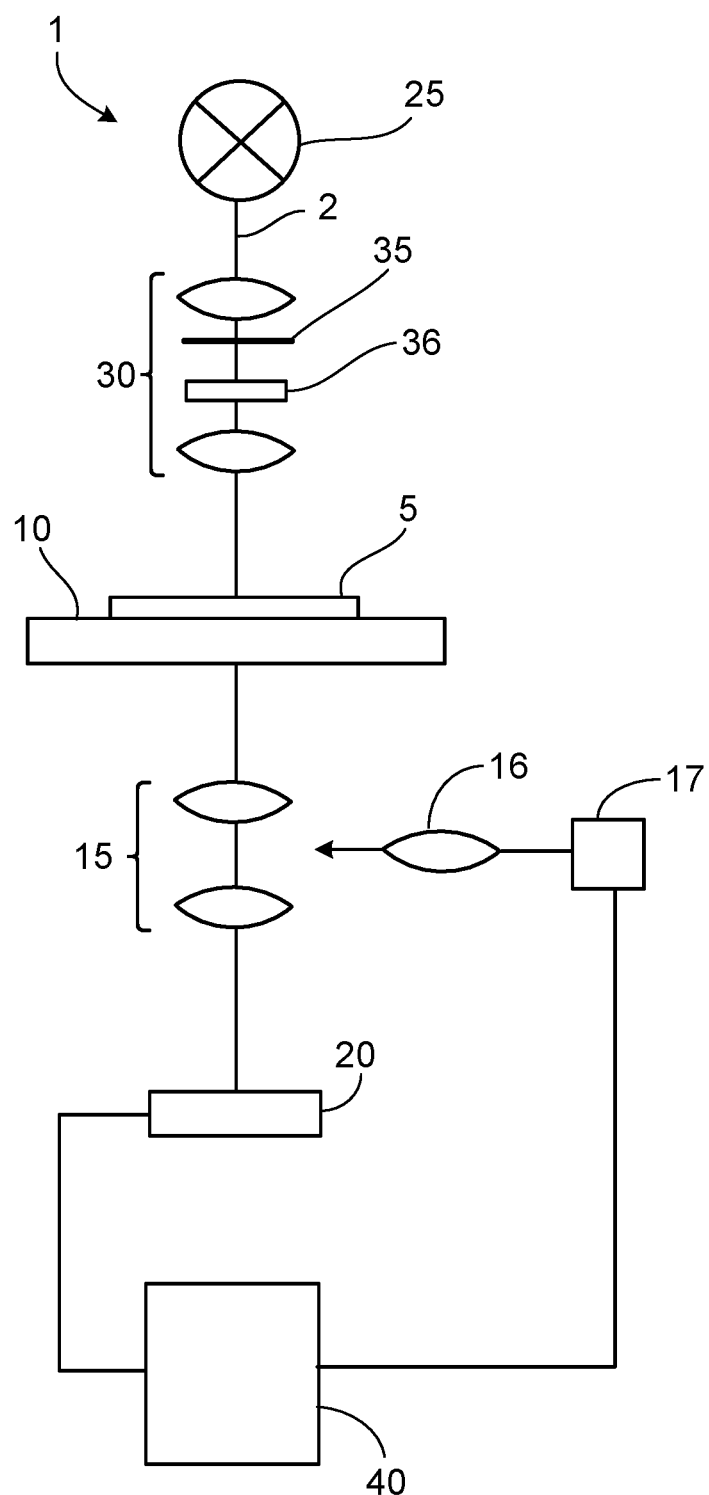
FIG. 1: shows a schematic illustration of the structure of a microscope.

The structure of a microscope 1, which is suitable for examining masks, will be explained on the basis of FIG. 1. The microscope 1 has a sample holder 10, on which the object 5 to be imaged lies, and a detector 20 implemented as a CCD chip (charge coupled device). A light source 25 illuminates the object 5 via an illumination optic 30, which has a pupil plane 35. Illumination settings can be set via a pupil filter, which is arranged in the pupil plane 35, and a polarizer 36. During the recording of the aerial images of the object 5 using the detector 20, illumination settings and polarization settings adapted to the structure are used.

An aerial image of the object 5 is generated via the imaging optic 15, having the optical axis 2, in the plane of the detector 20. For focusing, the imaging optic 15 is moved in the direction perpendicular to the X-Y plane, referred to as the Z direction, along the optical axis 2. The aerial image is read out by the computing unit 40, which is implemented as a computer. The aerial image is firstly provided as a data set or data structure in the operating memory of the computer. It can be stored as a graphic file on the hard drive of the computer. The data structure or the graphic file is a two-dimensional matrix which is constructed from pixels. The intensities of the pixels are represented by numeric values from 0 to 255. The image field on the mask is square, having an edge length of 10 µm. The detail of the recorded partial structure is determined by the image field.

To record an aerial image of the intensity distribution in the pupil plane 35 of the illumination optic 30, a Bertrand lens 16 is introduced into the beam path of the microscope 1 by a drive 17, controlled by the computing unit 40. The aerial image is stored in the memory of the computing unit 40 as a first matrix having constant resolution.

Microscopes such as the described microscope 1 are used for examining masks in lithography as a mask inspection microscope or as position measuring devices. The sample holder 10 is then implemented as a mask holder or stage. The object 5 to be examined is a mask.

The analysis of the mask and the assignment of structure types, measurement regions, and measuring tasks are performed using the design software CATS from Synopsis Inc.

The defect positions to be examined are specified in a position data set. These can have been determined by a mask inspection or hot spots of the structure can have been determined.

Firstly, structure types are specified, which are assigned to structural features. Structural features which represent measured variables are assigned threshold values or value ranges. These value ranges are specified nominal values or permissible tolerance ranges for the structure. Examples of structure types, structural features, and possible values and value ranges are provided in Table 1.

TABLE 1

| structural features | end-to-end (End-to-End) (MM) | contact hole (Contact Hole) (BOXROT) | lines and spaces (Lines and Spaces) (CDR) |
|---|---|---|---|
| tone (TONE) | opaque (OPAQUE) | transparent (CLEAR) | transparent (CLEAR) |
| contour (CONTOUR) | open (OPEN) | closed (CLOSED) | open (OPEN) |
| width (NM_WIDTH) | 0.09-2 µm | 0.08-0.5 µm | 0.5-2 µm |
| critical dimension (CD) | 0.09-0.6 µm | 0.11-0.5 µm | 0.19-0.35 µm |
| aspect ratio (ASPECT RATIO) | 1-60 | 1-3 | 2-11 |

The respective technical terms are specified between parentheses and also the designations in the design environment CATS. The numeric values are examples.

Figure 2A:
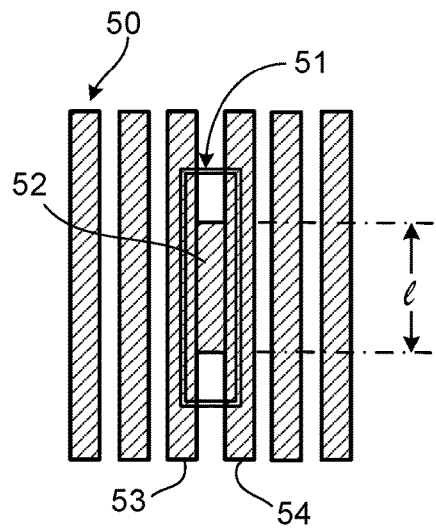
FIG. 2: shows a schematic illustration of examples of structure types having measurement regions.
Figure 2B:
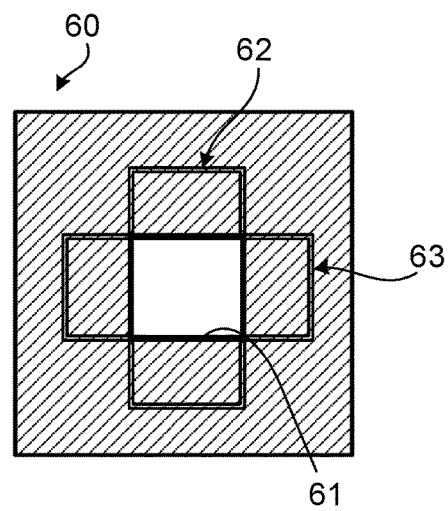
Figure 2C:
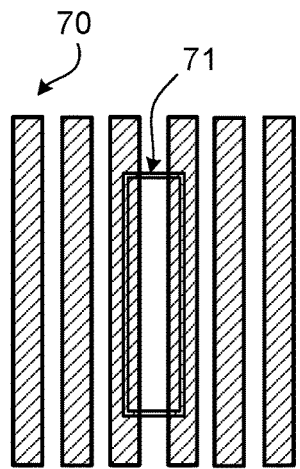

Each structure type is assigned a measurement region. This assignment of a specified structure type to the respective structure at a defect position is performed automatically by the CATS software. In this program, corresponding algorithms for image processing and analysis are implemented. Examples of structure types and assigned measurement regions are illustrated in FIGS. 2*a*, 2*b*, and 2*c*. Shaded areas represent light-opaque regions of the structure of a mask.

A detail 50 of a structure is shown in FIG. 2*a*. In the middle of the detail, an end-to-end structure is illustrated. The measurement region 51 is illustrated by a rectangle. The end-to-end structure is illustrated in this example as a line 52 of the length 1, which connects the two adjacent lines 53, 54 of the surrounding lines and spaces. The determination of the tone is performed in the center point of the measurement region 51.

In FIG. 2*b*, a detail 60 of a structure is shown, which has a contact hole 61. The measurement region is marked by two intersecting rectangles 62, 63, wherein the contact hole is arranged in the intersection point of the rectangles.

In FIG. 2*c*, a detail 70 of lines and spaces is shown. The assigned rectangular measurement region 71 extends over the space between two lines and approximately half of the adjoining lines.

Figure 3:
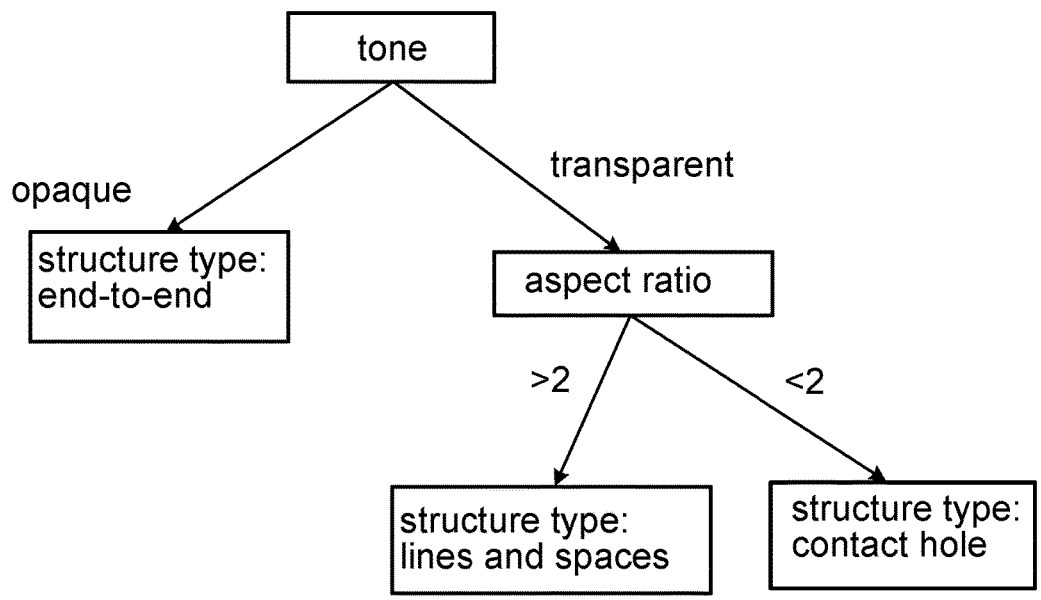
FIG. 3: shows a schematic diagram of an example of decision criteria of a correlation data set.
Figure 4:
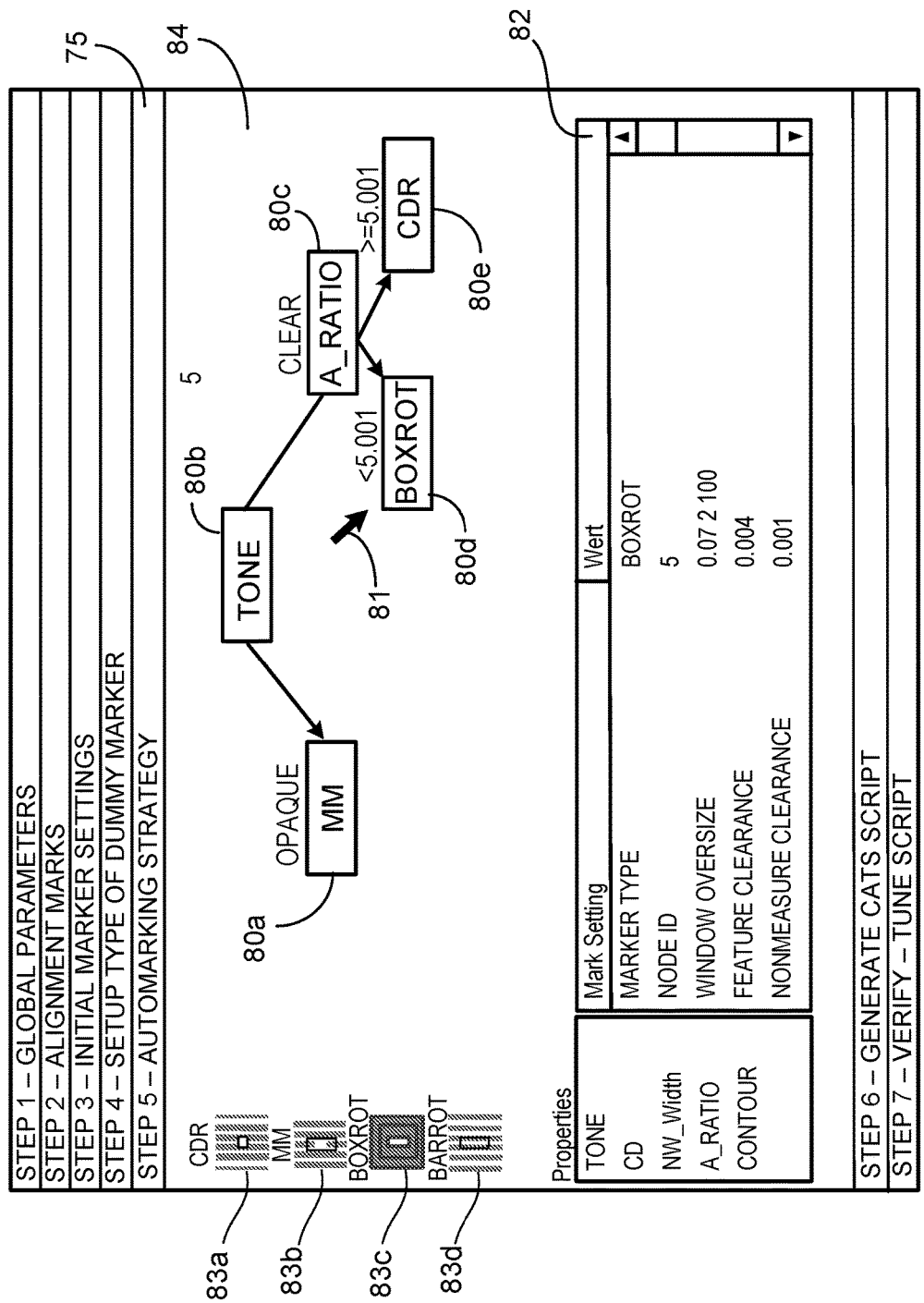
FIG. 4: shows a schematic diagram of a user interface for inputting decision criteria.

For the automatic assignment of the structure types to the defect positions, decision criteria are specified, which form a correlation data set. The decision criteria can have a hierarchical structure. An example of a decision hierarchy is illustrated in FIG. 3. In this case, decision nodes can be specified for structural features. At a decision node, a structural feature, for example, the tone, is specified and the decision about at least two alternative paths is made in dependence on the value of the structural feature. In the example of FIG. 3, in the case of the value "opaque" of the structural feature tonality, the structure type end-to-end is directly assigned. If the structural feature tonality has the value "transparent", in the next step the structural feature "aspect ratio" is then checked. A threshold value is specified here. If the value is less than the threshold value, the structure type lines and spaces is assigned, if the value is greater than the threshold value, the defect position is assigned the structure type contact hole.

In addition to threshold values, ranges of the values can also be specified as criteria. In addition to individual structural features, logical linkages of multiple structural features can also be specified as criteria.

A script, also referred to as a program or computer program, is prepared from the correlation data set in a script language of the design software CATS. This script enables an automatic assignment of the defect positions to the structure types by the computing unit.

Figure 5:
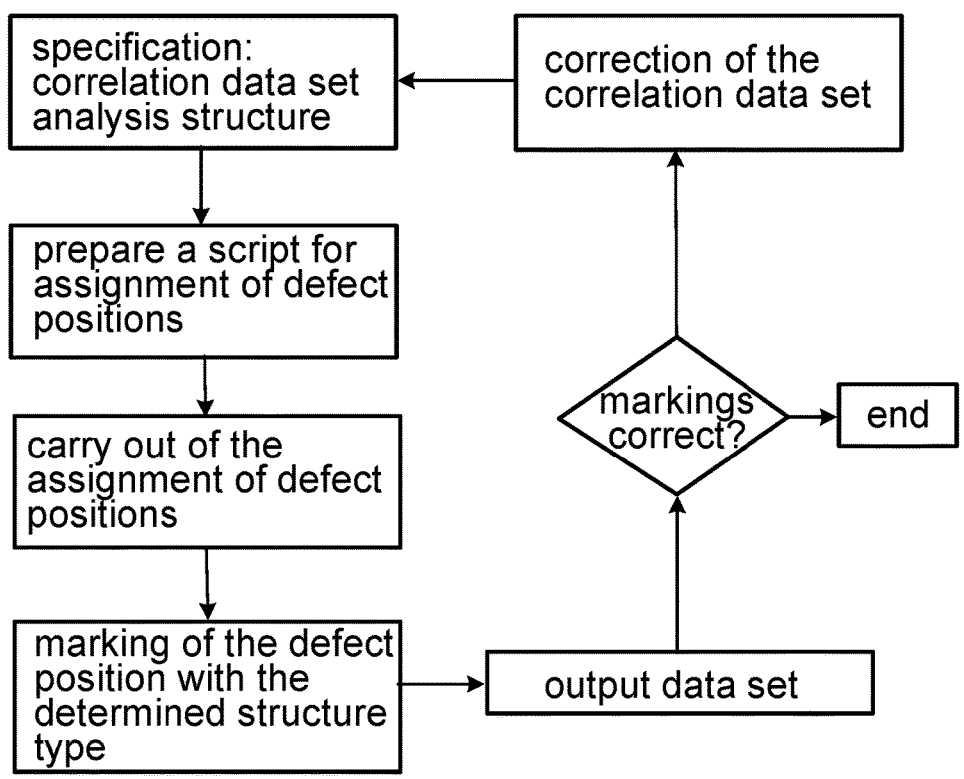
FIG. 5: shows a schematic diagram of the sequence of the method for optimizing decision criteria.

The correlation data set can be prepared with the aid of a graphically assisted user interface. Decision nodes can be specified and linked by the user by way of graphic elements. An example of a user interface is illustrated in FIG. 3. This user interface is displayed on a display screen of the computing unit when the program is executed on the computing unit. As an example, the same decision hierarchy is shown here which was already explained on the basis of FIG. 3. To prepare a decision node, firstly a pictogram of the desired structural feature is selected from the illustrated pictograms 83a, 83b, 83c. The selection is performed by clicking the pictogram using a computer mouse (mouse in short hereafter) and pulling it into the strategy region 84 of the program window 75. The identification of the pictograms follows the abbreviations, which are also specified in Table 1 and are routine in technical circles, for the respective structural features. Multiple decision nodes are arranged in accordance with the desired hierarchy in the strategy region 84 of the program window 75. As soon as the symbol of a decision node is selected by clicking using the mouse, a criteria window 82 opens. The values of the structural features and the decisions following therefrom are specified in this criteria window 82. It is specified which further structural feature is checked if the value of the structural feature fulfills the specified value or lies within a specified value range. It can also be specified which structure type is assigned on the basis of a decision. When the decision nodes, the decision criteria, and the linkages are input, the script preparation is performed automatically by the computing unit. This method is illustrated in FIG. 5. To check the decision criteria, the performed assignments in the output data set are checked. This is preferably performed for a representative sample of all defect positions. By analyzing the incorrect assignments, the decision criteria, for example, the threshold values, are optimized. This optimization is repeated until a defect-free assignment of structure types is performed for all defect positions.

Each structure type is assigned a measuring task. The measuring tasks can comprise the determination of one or more variables from measurements using a probe or multiple probes within the measurement region. Examples of structure types having assigned measuring tasks and the steps to be carried out are provided in Table 2. The probe to be used is a WLCD device in these examples.

TABLE 2

| structure type | measuring task | steps of the measuring task |
| --- | --- | --- |
| end-to-end (End-to-End) (MM) | EvalMinMaxCD | local image alignment threshold value determination threshold value application contouring detection of min/max value in measurement direction report measured value and coordinates |
| contact hole (Contact Hole) (BOXROT) | EvalContactHole | local image alignment threshold value determination threshold value application contouring detection of diameter in X and Y directions (CD value) report measured value |

TABLE 2-continued

| structure type | measuring task | steps of the measuring task |
| --- | --- | --- |
| lines and spaces (Lines and Spaces) (CDR) | EvalCD | local image alignment threshold value determination threshold value application contouring determination of average distance in measurement direction over non-measurement direction report measured value (CD value) |

To carry out the assignment of the structure types to the defect positions, in a first step, the values of the structural features of the structure at the defect positions are determined. For this purpose, a special structure type having a special measurement region, which is exclusively used to determine the values of the structural features is assigned to the defect positions. This structure type is referred to hereafter as an analysis structure. The determination of the values of the structural features is performed by the CATS software. One of the mentioned structure types with the associated measurement region can also be used as a special structure type, for example, the structure type contact hole. The values of all structural features for all defect positions are provided as a data set after this step.

In one variant of the method, the structural features are determined by analysis of an aerial image, which was simulated from the structure at the defect position. The simulation of aerial images is performed by methods as are described in the publication: H.H. Hopkins: On the diffraction theory of optical images. Proceedings of the Royal Society of London. Series A, Mathematical and Physical Sciences, 217 (1130): 408-432, 1953. For example, the program MicroSim is available for the simulation of aerial images of masks. The simulation is performed proceeding from the structure specifications of the mask, the mask design. The program MicroSim is described, for example, in: M. Totzeck, "Numerical simulation of high-NA quantitative polarization microscopy and corresponding near-fields," Optik, 112 (2001) 381-390, (MicroSim-Software, University of Stuttgart). During the simulation, the conditions of the imaging of the microscope 1, for example, the numeric aperture, wavelength, polarization, and degree of coherence of the illumination or the illumination radiation, etc., are taken into consideration.

In a further variant of the method, the structural features can be produced by analysis of an aerial image, which was recorded from a defect-free mask. The comparison of structural features of one measurement region to a defect-free measurement region of the same mask can also be performed.

Figure 6:
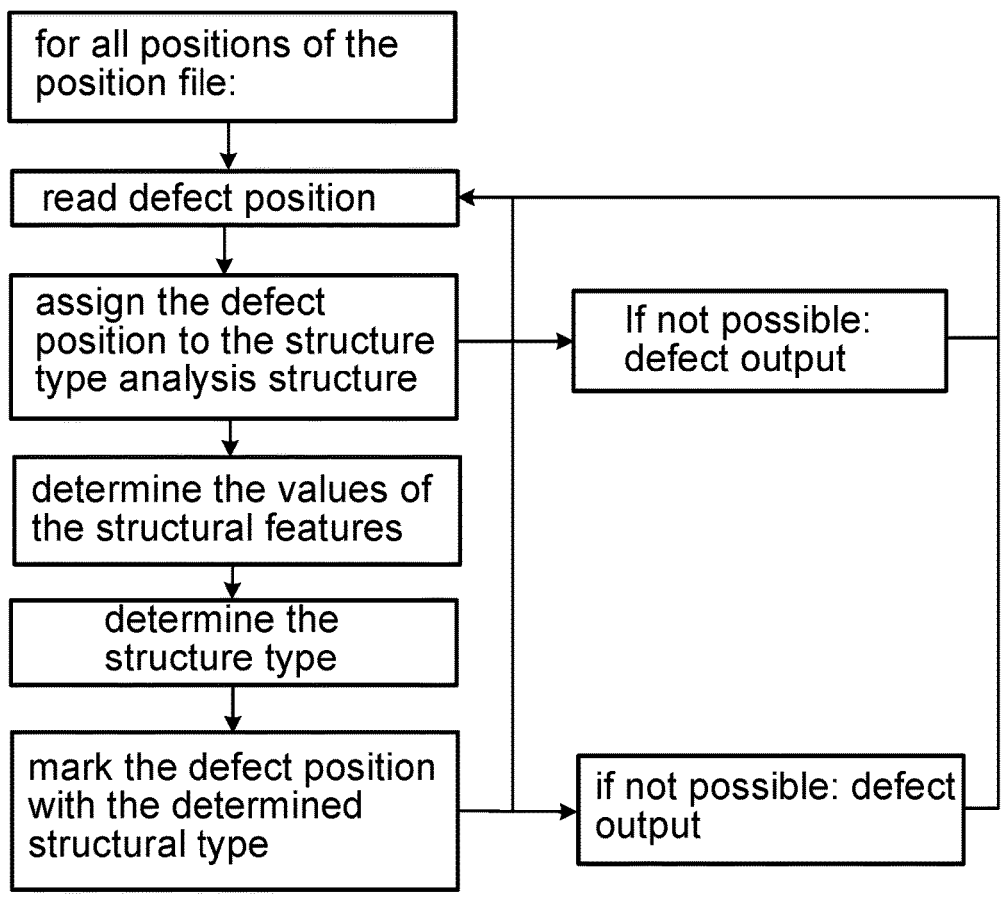
FIG. 6: shows a schematic diagram of the sequence of the assignment of structure types to defect positions.

In the next step, the CATS script is processed by the computing unit. The measuring tasks determined for the defect positions are then, in a manner controlled by the computing unit, carried out by a microscope 1 or another provided measuring device. The method is illustrated in FIG. 6. If the automatic determination of structural features or the assignment of a structure type is not possible for a defect position, the output takes place into a defected data set. Manual post-processing can then be carried out for these defect positions.

Examples of measuring tasks are provided in Table 2. The steps specified therein will be explained hereafter.

"Local image alignment" refers to a method for aligning the measured aerial image of a mask to a simulated aerial image. The simulated aerial images is prepared at the position of the mask structure of the measured aerial image, as described above, from the structure of the mask. The aerial image is simulated in the region of the image field of the microscope 1. By way of this measure, the precision of the correspondence of the measured structure and the structure specified in the structure file is increased. This correspondence is limited after the measurement of the aerial image by the microscope 1 by the precision of the positioning of the stage 10. The precision of the measurement is increased by the increased precision of the correspondence of the positions.

The "threshold value determination" refers to a method for defining the threshold value (threshold) at which the following measurements are to be carried out. In the simplest case, an intensity value can be specified here. In one variant, to determine the threshold value, the maximum intensity within the measurement region can be determined. The threshold value is then specified as a fraction of the maximum intensity. A fraction of the difference of the maximum intensity and the minimum intensity within the measurement region can also be determined. The threshold value is then specified as a fraction of this difference.

In a further variant of the threshold value determination, the threshold value is determined at which the fundamental measured value corresponds to a specified value. A target CD is specified here, for example. This is a target value of a line width, which is referred to as the critical dimension (CD). The target CD is typically specified for a structure. In the determination of multiple measured values, the determined threshold value relates to the average of all measured values.

"Intensity threshold value application" refers to the application of the determined threshold value to the measured aerial image. This comprises, for example, the determination of values of the critical dimension (CD). This also comprises the "contouring".

The "contouring" refers to the representation of the contour of the aerial image on the intensity value of the determined threshold value. This is used to visualize the results. The "contouring" can be carried out in one variant of the method as a step for determining measured values, for example, the critical dimension.

"Detection min/max value in measurement direction" refers to a method for determining the maximum and/or the minimum critical dimension within a measurement region. The critical dimension is determined in the measurement direction (the direction along the lines and spaces) at all possible positions. The maximum value or the minimum value and the coordinates thereof are then determined from all determined values.

"Detection of diameter in X and Y directions" refers to the measurement of the edge lengths of a contact hole both in the X direction and also in the Y direction. In one variant, the diameter of a circle can be calculated, which would have the same surface area as the contact hole. This value is used as a measured value for the quality of the structure on the mask.

"Determination of average distance in measurement direction over non-measurement direction" refers to the determination of, for example, the critical dimension in the measurement direction (the direction along the lines and spaces) at all possible positions. The average is then calculated from all determined values.

"Report of measured value and coordinates" refers to the output of the determined measured values and, if necessary, the coordinates for further processing by the computing unit. The output can be performed in an output data set. It can be stored as a file.

The invention claimed is:

1. A method for examining a mask comprising:
   providing a position data set having defect positions of the mask to be examined, in which the defect positions are determined prior to examining the mask, and the defect positions represent positions on the mask where defects may occur;
   providing a structure data set having the structure of the mask;
   providing structural features of the mask, the values of which are to be determined; and at each defect position:
      determining the values of the specified structural features of the structure by using a computing unit;
      selecting a measuring task from a plurality of measuring tasks based on specified decision criteria and the determined values of the structural features of the structure by using the computing unit, in which the values of the structural features are determined at the defect position that represents one of the positions on the mask where a defect may occur; and
      carrying out the determined measuring task in a manner controlled by the computing unit.

2. The method according to claim 1, wherein a correlation data set having decision criteria is provided, which comprises an assignment of structural features of the structure to the measuring task.

3. The method according to claim 1, wherein the determination of the measuring tasks is performed by a script of the CATS software, which is executed in the computing unit.

4. The method according to claim 1, wherein a script for determining the measuring tasks is prepared from the correlation data set by the computing unit.

5. The method according to claim 1, wherein a measuring task comprises recording an aerial image using a microscope.

6. The method according to claim 1, wherein the defect positions of the position data set are determined by carrying out a mask inspection.

7. The method according to claim 1, wherein the defect positions of the position data set comprise hot spots of the structure.

8. The method according to claim 1, wherein each defect position is assigned a measurement region.

9. The method according to claim 8, wherein to determine the structural features of a structure from the respective structure data set, an aerial image of the assigned measurement region is simulated, wherein the structural features are determined by an analysis of the aerial image by a computing unit.

10. The method according to claim 1, wherein at least one of the following structural features is determined: critical dimension, tone, edge length, length of a line, aspect ratio of length and width.

11. The method according to claim 1, wherein at least the following structure types are assignable: lines and spaces, contact hole, end-to-end.

12. A microscope comprising:
    a computing unit configured to carry out the method according to claim 1,
    an imaging optic for imaging the structure of the mask at the defect positions, and a detector for recording an aerial image of the structure of the mask at the defect positions.

13. A microscope comprising a computing unit configured to carry out the method according to claim 2, an imaging optic for imaging the structure of the mask at the defect positions, and a detector for recording an aerial image of the structure of the mask at the defect positions.

14. A microscope comprising a computing unit configured to carry out the method according to claim 3, an imaging optic for imaging the structure of the mask at the defect positions, and a detector for recording an aerial image of the structure of the mask at the defect positions.

15. A microscope comprising a computing unit configured to carry out the method according to claim 4, an imaging optic for imaging the structure of the mask at the defect positions, and a detector for recording an aerial image of the structure of the mask at the defect positions.

16. A microscope comprising a computing unit configured to carry out the method according to claim 5, an imaging optic for imaging the structure of the mask at the defect positions, and a detector for recording an aerial image of the structure of the mask at the defect positions.

17. A microscope comprising a computing unit configured to carry out the method according to claim 6, an imaging optic for imaging the structure of the mask at the defect positions, and a detector for recording an aerial image of the structure of the mask at the defect positions.

18. A microscope comprising a computing unit configured to carry out the method according to claim 7, an imaging optic for imaging the structure of the mask at the defect positions, and a detector for recording an aerial image of the structure of the mask at the defect positions.

19. A microscope comprising a computing unit configured to carry out the method according to claim 8, an imaging optic for imaging the structure of the mask at the defect positions, and a detector for recording an aerial image of the structure of the mask at the defect positions.

20. A microscope comprising a computing unit configured to carry out the method according to claim 10, an imaging optic for imaging the structure of the mask at the defect positions, and a detector for recording an aerial image of the structure of the mask at the defect positions.

* * * * *

UNITED STATES PATENT AND TRADEMARK OFFICE
CERTIFICATE OF CORRECTION

| | |
|---|---|
| PATENT NO. | : 9,869,640 B2 |
| APPLICATION NO. | : 14/563259 |
| DATED | : January 16, 2018 |
| INVENTOR(S) | : Thomas Trautzsch, Ute Buttgereit and Thomas Thaler |

It is certified that error appears in the above-identified patent and that said Letters Patent is hereby corrected as shown below:

On the Title Page

Column 1, (30) Foreign Application Priority Data, Line 1, delete "10201302075" and insert -- 102013020705.3 --

Signed and Sealed this
Eleventh Day of June, 2019

Andrei Iancu
*Director of the United States Patent and Trademark Office*